(12) United States Patent
Davis et al.

(10) Patent No.: US 7,598,643 B2
(45) Date of Patent: Oct. 6, 2009

(54) MOTOR WITH ELECTRODYNAMICALLY AND HYDRODYNAMICALLY SUPPORTED ROTOR

(76) Inventors: William D. Davis, P.O. Box. 1093, Dripping Springs, TX (US) 78620; David M. Lancisi, 104 Luttrel Ct., Folsom, CA (US) 95630

( * ) Notice: Subject to any disclaimer, the term of this patent is extended or adjusted under 35 U.S.C. 154(b) by 0 days.

(21) Appl. No.: 10/556,861

(22) PCT Filed: May 15, 2003

(86) PCT No.: PCT/US03/15155

§ 371 (c)(1),
(2), (4) Date: Nov. 14, 2005

(87) PCT Pub. No.: WO2004/106746

PCT Pub. Date: Dec. 9, 2004

(65) Prior Publication Data
US 2007/0053781 A1    Mar. 8, 2007

(51) Int. Cl.
*H02K 7/09*    (2006.01)
(52) U.S. Cl. .................. 310/90.5; 310/67 R; 310/90
(58) Field of Classification Search ............. 310/67 R, 310/90.5, 62–63, 90; 417/420, 424
See application file for complete search history.

(56) References Cited

U.S. PATENT DOCUMENTS

| | | | |
|---|---|---|---|
| 4,036,565 A * | 7/1977 | Becker ................. | 417/420 |
| 4,579,508 A | 4/1986 | Tsumaki et al. | |
| 5,237,229 A | 8/1993 | Ohishi | |
| 5,254,966 A | 10/1993 | Solar | |
| 5,256,637 A | 10/1993 | Rao | |
| 5,471,105 A | 11/1995 | Clifton et al. | |

(Continued)

FOREIGN PATENT DOCUMENTS

DE    3243641 A1    5/1984

(Continued)

OTHER PUBLICATIONS

"PMB Description", Institute of Robotics -Group of Passive Magnetic Bearings, Swiss Federal Institute of Technology-Lausanne (Oct. 1, 2000) http://dmtwww.epfl.ch/~jsandtne/GPMB/description1.htm.

(Continued)

*Primary Examiner*—Thanh Lam
(74) *Attorney, Agent, or Firm*—Davis & Associates; William D. Davis

(57) ABSTRACT

An apparatus includes a rotor, a stator, and a plurality of magnets forming bearing poles coupled to a selected one of the stator or the rotor. The apparatus further includes a plurality of shorted coils coupled to the other of the stator and the rotor. The plurality of bearing poles and shorted coils cooperate to form an electrodynamic bearing during rotation of the rotor. The electrodynamic bearing supports the rotor either axially or radially during operation. Hydrodynamic bearing surfaces are provided for generating a hydrodynamic bearing between the rotor and stator. The plurality of magnets may comprise a plurality of distinct magnetic elements or a single element comprising a plurality of distinct magnetic domains. The plurality of distinct magnetic elements or domains may be arranged to form a Halbach array.

19 Claims, 13 Drawing Sheets

U.S. PATENT DOCUMENTS

| | | | |
|---|---|---|---|
| 5,607,329 | A | 3/1997 | Cho |
| 5,695,471 | A | 12/1997 | Wampler |
| 5,840,070 | A | 11/1998 | Wampler |
| 5,925,952 | A | 7/1999 | Bichler et al. |
| 5,928,131 | A | 7/1999 | Prem |
| 6,015,272 | A * | 1/2000 | Antaki et al. ............... 417/356 |
| 6,050,782 | A | 4/2000 | Lembke |
| 6,080,133 | A | 6/2000 | Wampler |
| 6,111,332 | A | 8/2000 | Post |
| 6,194,798 | B1 | 2/2001 | Lopatinsky |
| 6,227,797 | B1 | 5/2001 | Watterson et al. |
| 6,227,817 | B1 | 5/2001 | Paden |
| 6,227,820 | B1 | 5/2001 | Jarvik |
| 6,244,835 | B1 | 6/2001 | Antaki et al. |
| 6,250,230 | B1 | 6/2001 | Post |
| 6,304,015 | B1 | 10/2001 | Filatov et al. |
| 6,527,699 | B1 | 3/2003 | Goldowsky |
| 2002/0102169 | A1 | 8/2002 | Wampler |
| 2003/0007879 | A1 | 1/2003 | Chen |

FOREIGN PATENT DOCUMENTS

| | | |
|---|---|---|
| WO | WO 98/32981 A1 | 7/1998 |
| WO | WO 99/12587 A1 | 3/1999 |
| WO | WO 99/28626 A1 | 6/1999 |
| WO | WO 2004/106746 A1 | 12/2004 |

OTHER PUBLICATIONS

"PMB Photos", Institute of Robotics-Group of Passive Magnetic Bearings, Swiss Federal Institute of Technology-Lausanne (Oct. 1, 2000) http://dmtwww.epfl.ch/—jsandtne/GPMB/photos1.htm.

"PMB Projects: Passive Electromagnetic Suspension for Rotor Applications", Institute of Robotics-Group of Passive Magnetic Bearings, Swiss Federal Institute of Technology -Lausanne (Oct. 1, 2000) http://dmtwww.epfl.ch/~jsandtne/GPMB/project1.htm.

Coey, Michael, et al. "Magnets, Markets, and Magic Cylinders", Industrial Physicist (Sep. 1998), p. 34-36.

* cited by examiner

MOTOR WITH ELECTRODYNAMICALLY AND HYDRODYNAMICALLY SUPPORTED ROTOR

This is a national stage application under 35 U.S.C. 371 of PCT application number PCT/US03/15155 having a May 15, 2003 international filing date and claims priority to U.S. patent application Ser. No. 10/007,803 filed Nov. 13, 2001, now U.S. Pat. No. 6,641,378.

FIELD OF THE INVENTION

This invention relates to the field of pump design. In particular, this invention is drawn to bearings supporting pump impellers.

BACKGROUND OF THE INVENTION

Traditional dynamic pumps have a pumping component and a drive component. The pumping component includes an impeller supported by mechanical contact bearings. Mechanical energy is transferred from the drive component to the impeller of the pumping component through a shaft. A shaft seal in the pumping component permits rotation of the shaft while preventing leakage around the shaft.

Shaft seals are prone to failure due to continuous mechanical wear during operation of the pump. Mechanical contact bearings supporting the impeller are also prone to failure. The pumped fluid may adversely affect the life expectancy of the bearings. For example, the mechanical contact bearings and seal may be particularly susceptible to failure when in contact with caustic materials. Alternatively, the bearings may damage the fluid being pumped. Contact bearings, for example, may result in increased levels of hemolysis and thrombosis in blood pump applications.

Some recent pump designs have integrated the pump and drive components into a single unit so that the pump impeller is also the motor rotor, thus eliminating the need for a transmission shaft to supply power to the impeller. Such designs eliminate the need for shaft seals. Examples of pumps with a combination impeller/rotors may be found in U.S. Pat. No. 5,607,329 of Cho, et al. (marine propulsor), U.S. Pat. No. 5,695,471 of Wampler and PCT publication WO 99/12587 of Woodard, et al. (blood pumps).

Some of these pump designs also incorporate passive magnetostatic bearing (PMB) or active magnetic bearing (AMB) systems or other non-contacting bearing mechanisms (e.g., hydrodynamic bearings) in lieu of mechanical contact bearings to stabilize the impeller axially and/or radially. Without mechanical bearings to wear out, these non-contacting bearing mechanisms eliminate disadvantages associated with the mechanical contact bearings.

PMB architectures are characterized by the use of opposing sets of permanent magnets arranged to repulse each other. The bearings are thus magnetostatic bearings. For example, Wampler discloses radial magnetostatic bearings using concentric sets of stacked magnetic elements of alternating magnetization. Radial impeller support is provided by locating one set of magnetic elements in the stator and another set in the impeller such that the first and second sets are concentric and coaxially aligned. The concentric stacks of permanent magnets co-operate to form a radial PMB. The repulsive magnetostatic forces are substantially constant independent of pump speed.

One disadvantage of this design is that each magnet in a stack is constantly exposed to a significant de-magnetizing field due to the close proximity of the adjacent magnets in the stack. Another disadvantage of this design is that the use of axially alternating magnetic rings results in a number of points of axial metastability which may create pump control or efficiency issues. The passive magnetostatic bearings can create significant axial bearing load issues for impellers with a radial PMB. Similarly, impellers with an axial PMB may suffer from significant radial bearing load issues. These loading forces result in a less power efficient pump.

Active magnetic bearing systems are characterized by the use of permanent magnets, electromagnets, position feedback information, and controllers as illustrated by U.S. Pat. No. 6,227,817 B1 of Paden. The impeller is stabilized with respect to one or more axes by a controlled interaction between the magnets and electromagnets. The electromagnets are dynamically controlled by the controller based on the position feedback information and sophisticated control algorithms. Position of the impeller is controlled by varying the current through the windings forming the electromagnets. Due to the dynamic nature of the control elements, the impeller position can be controlled with greater precision. In addition, active magnetic bearing systems can be incorporated into the drive such that the electromagnets are serving to both drive and support the rotor.

The PMB system does not require position feedback or power to operate. In contrast, an AMB will fail in the event of a power interruption, computational error, sensing error along any axis, etc. AMB systems are thus inherently unstable. AMB systems also require significant computational resources for position control. The use of AMB systems introduces multiple points of failure which may be unacceptable for some pump applications (e.g., implantable pumps).

SUMMARY OF THE INVENTION

A pump apparatus includes an impeller, a stator, and a plurality of permanent magnets forming bearing poles. The bearing poles are coupled to a selected one of the stator or the impeller. A plurality of shorted coils is coupled to the other of the stator and the impeller. The bearing poles and the shorted coils co-operate to form an electrodynamic bearing during rotation of the impeller.

The electrodynamic bearing supports the impeller either axially or radially during operation of the pump. Currents induced into each coil by a single bearing pole or by a plurality of bearing poles substantially simultaneously produce an electrodynamically generated magnetic field that repels the inducing bearing pole(s) when the impeller is rotating. In one embodiment, if each shorted coil interacts with k bearing poles substantially simultaneously, the k bearing poles are distributed at equidistant mechanical angles of $$\frac{2\pi}{k}$$

radians about the impeller axis of rotation. Bearing poles and/or motor poles may be composed of individual magnetic elements, each element having substantially the same magnetization vector throughout. Alternatively, distinct bearing poles and/or motor poles may be formed by creating individual magnetic domains within a single element.

Other features and advantages of the present invention will be apparent from the accompanying drawings and from the detailed description that follows below.

BRIEF DESCRIPTION OF THE DRAWINGS

The present invention is illustrated by way of example and not limitation in the figures of the accompanying drawings, in which like references indicate similar elements and in which.

DETAILED DESCRIPTION

Figure 1:
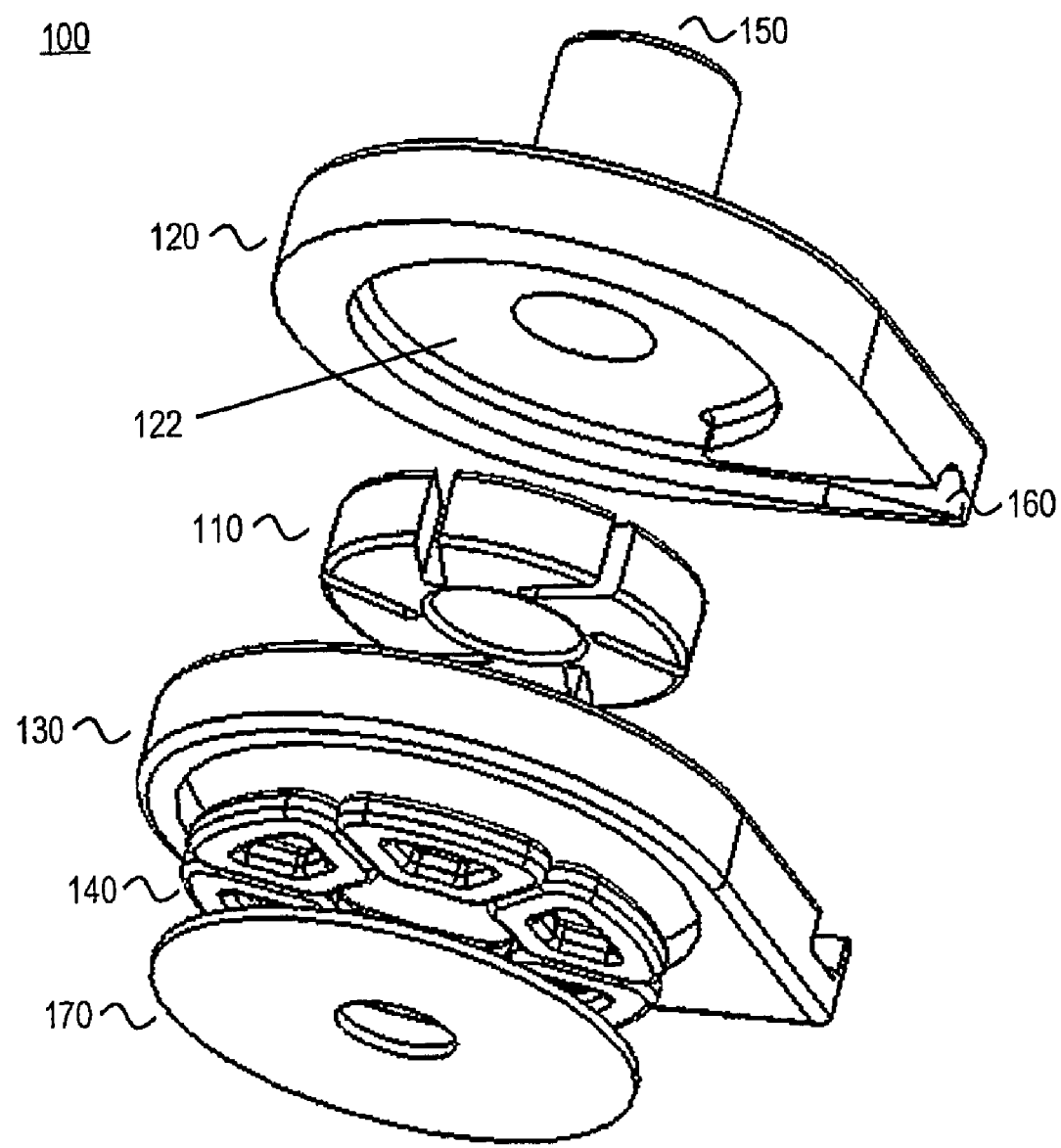
FIG. 1 illustrates one embodiment of a centrifugal pump.

FIG. 1 illustrates one embodiment of a centrifugal pump 100 providing radial support for the impeller 110 through the use of magnetic bearings. The pump includes a top housing portion 120 and a bottom housing portion 130. When assembled the top and bottom housing portions define a volute pumping chamber 122. Rotation of impeller 110 drives the working fluid from the pump inlet 150 to the pump outlet 160.

Centrifugal pump 100 utilizes an axial flux gap motor architecture. When assembled, the top and bottom housing portions serve as a motor stator. The motor windings 140 are disposed in the stator. The impeller serves as a motor rotor and includes a plurality of permanent magnets forming motor poles. The motor poles are arranged to co-operate with the motor windings to drive the impeller and thus achieve a pumping action. Back iron 170 serves to concentrate the flux generated by the windings 140.

The pump further includes a spindle protruding from the base of the pumping chamber. The spindle is not illustrated in FIG. 1 to avoid obscuring the remainder of the pump. The impeller 110 rotates about the spindle. The spindle thus forms a part of the stator. In this embodiment, the impeller 110 contains one portion of the radial magnetic bearing. The spindle carries another portion of the radial magnetic bearing. The impeller and spindle bearing portions co-operate to provide radial support for the impeller.

Figure 2:
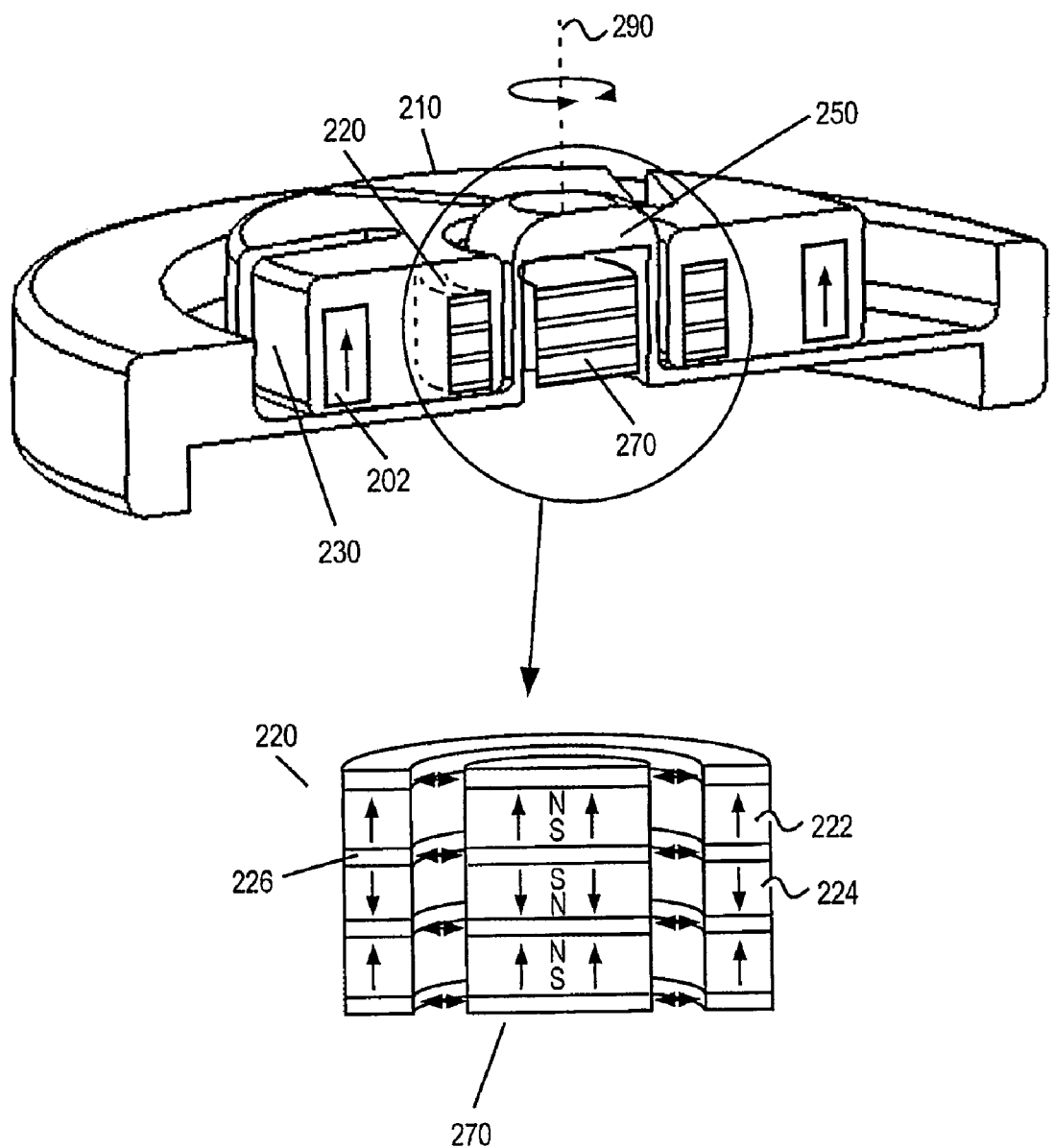
FIG. 2 illustrates one embodiment of an impeller with a radial passive magnetic bearing (PMB).

FIG. 2 illustrates one embodiment of an impeller 210 with a radial passive magnetic bearing using concentric stacked permanent magnets. One set of ring or disk shaped permanent magnets 270 is retained by the stator/spindle 250 and a ring shaped set 220 is retained by the impeller 210. The impeller portion of the magnetic bearings are disposed within the impeller such that they are coaxially aligned with the axis of rotation 290 and encompass the center of the impeller. The stator set is supported by the spindle 250 protruding from the base of the volute. In this embodiment, the impeller also includes permanent magnets (e.g., motor pole 202) disposed within the blades (e.g., 230). The latter set of permanent magnets co-operate with the motor windings to drive the impeller.

Each stacked set of magnets is arranged so that they form a coaxially aligned set of magnetic cylinders of alternating opposing magnetization along the axis of rotation. If a selected magnetic element 222 in a stack has a magnetic vector parallel to the axis of rotation 290 and pointing a first axial direction (an "N" orientation), the adjacent magnet(s) (e.g., 224) have a magnetic vector parallel to the axis of rotation 290 and pointing 180° from the first axial direction (an "S" orientation). Each magnetic element in stack 220 is separated from its neighbor by a flux re-directing separator ring 226. Similarly, each magnetic element in stack 270 is separated from its neighbor by a flux-redirection separator disk or ring. In one embodiment, the separators are ferrous. The separators serve to re-direct and concentrate the magnetic flux radially. Proper alignment of the inner 270 and outer 220 stacks results in mutually repulsive forces between the inner and outer cylinders.

The impeller is radially supported by passive magnetostatic forces between the spindle set of magnets about which the impeller set of ring shaped magnets rotates. The concentric sets of stacked rings form a radial magnetostatic bearing and provide substantially the same radial force regardless of impeller rotational speed.

One disadvantage of this design is the change in magnetic flux along the axis of rotation 290. The magnetic field varies sharply because adjacent rings have magnetic vectors that have a 180° phase difference. The sharply varying magnetic field results in axial loading and multiple points of metastability. Another disadvantage of this design is that individual magnetic rings are continuously subjected to the demagnetizing fields of neighboring magnetic rings. Finally, due to the use of a magnetostatic bearing, any loading forces created by the bearing are present substantially independently of the impeller rotational speed. PMBs, however, may be designed to be inherently stable at least along a single axis. No power or control signals are required for the bearing to maintain integrity about the chosen axis.

One set of magnets may be replaced with electromagnetic windings to achieve the same affect. The windings are energized to produce a magnetic field and thus achieve the same effect as passive magnetic bearings. Depending upon the design, the electromagnetic windings may achieve control along more than a single axis. This approach requires greater computational capabilities because the position of the impeller must be monitored to determine the extent to which the windings should be energized to accommodate various loading forces. This type of bearing is referred to as an active magnetic bearing (AMB). Active magnetic bearings are inherently unstable. Power and proper control signals are required at all times for the bearing to maintain integrity.

An alternative magnetic bearing design uses a set of permanent magnets and a set of shorted coils. This magnetic bearing relies on the interaction between a plurality of permanent magnets and shorted coils when the impeller is rotating. The shorted coils are arranged such that the permanent magnets induce a current in the shorted coils due to relative movement between the magnets and the coils when the impeller is rotating. The current in the shorted coils generates a magnetic field that tends to oppose the magnetostatic field of the inducing permanent magnet. Instead of a passive magnetostatic bearing or an active magnetic bearing, the bearing mechanism results from self-induced electrodynamic forces. Such magnetic bearings are referred to as electrodynamic or eddy current bearings. The bearings are still "passive" in nature given that no external control signals or power is required to maintain integrity of the bearing.

Figure 3:
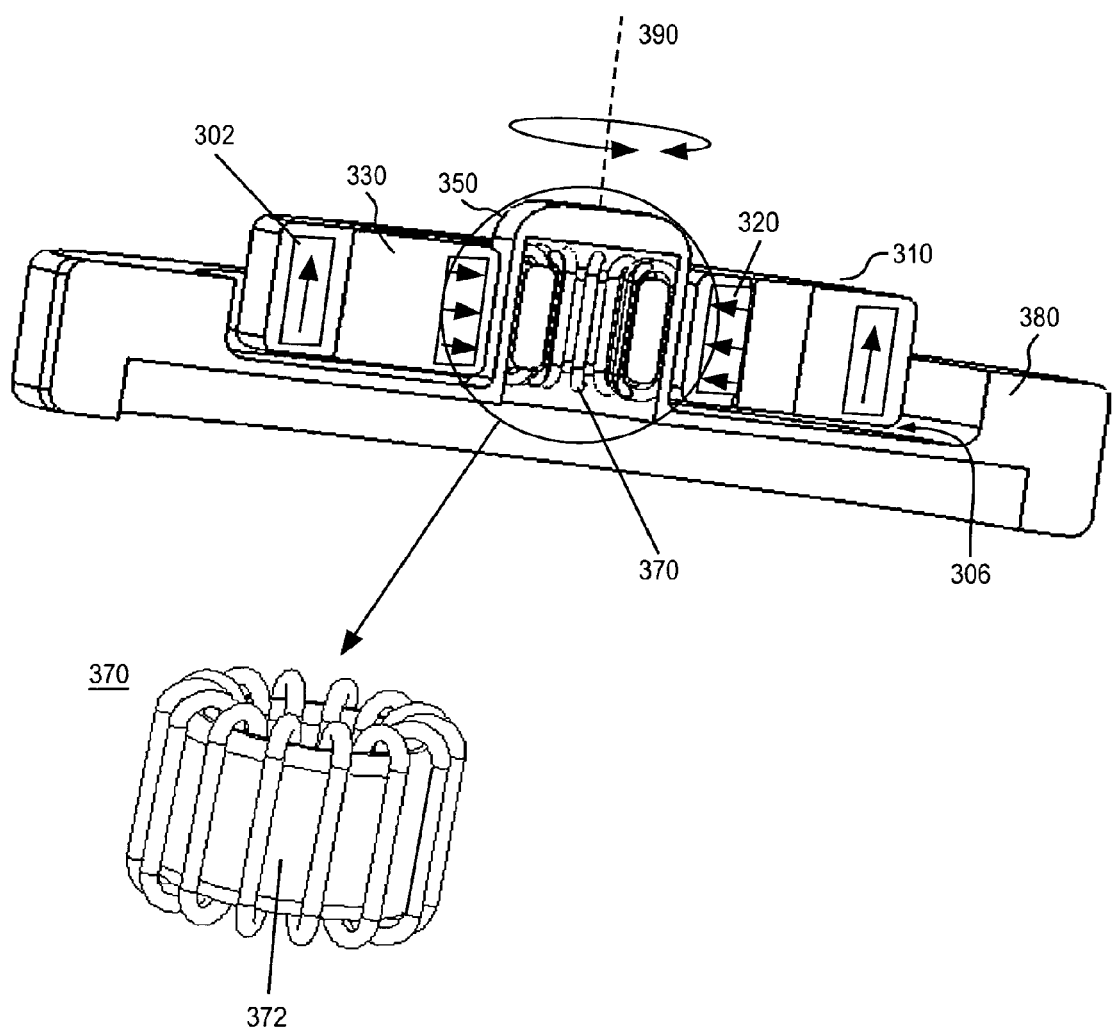
FIG. 3 illustrates one embodiment of an impeller with a radial electrodynamic bearing.

FIG. 3 illustrates an alternative embodiment of an impeller 310 incorporating a radial electrodynamic bearing. The impeller includes a plurality of permanent magnets 320 for the radial bearing as well as permanent magnets 302 forming the drive magnets. The bearing magnets 320 should be positioned so as not to interfere with the pump drive component formed by the motor windings and the drive magnets 302. In the illustrated embodiment, the drive magnets and bearing magnets are disposed within blades (e.g., 330) of the impeller 310. As the impeller rotates about axis 390, the bearing magnets create a time varying magnetic field that induces currents and corresponding repulsive magnetic forces in the shorted coils 370 within the spindle 350. The spindle forms a portion of the motor stator 380. In one embodiment, each shorted coil is wound around ferrous material 372.

Figure 4:
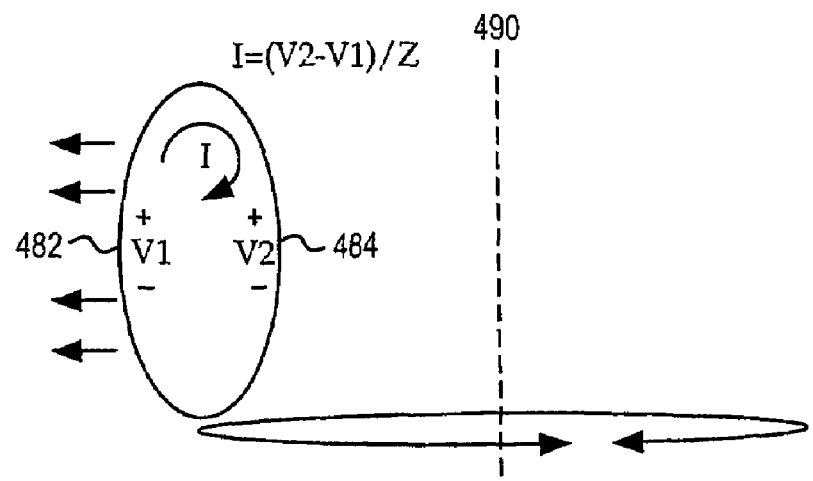
FIG. 4 illustrates an electrical model of a shorted coil illustrated in FIG. 3.

FIG. 4 illustrates an electrical model 480 of a single shorted coil of the radial bearing of FIG. 3. The electrical model illustrates the current and voltages induced in the shorted coil by the time-varying magnetic field created by the rotating impeller 310. As the impeller rotates about axis 490, a voltage differential develops between coil portion 482 and 484. The voltage differential results in a current, I, and a corresponding magnetic field which opposes the inducing magnetic field thus establishing the radial magnetic bearing.

When the impeller is rotating, only one side of each coil of coil assembly 370 is exposed to inducing bearing poles. Generally, current will be flowing in each coil as long as the impeller is rotating.

Figure 5:
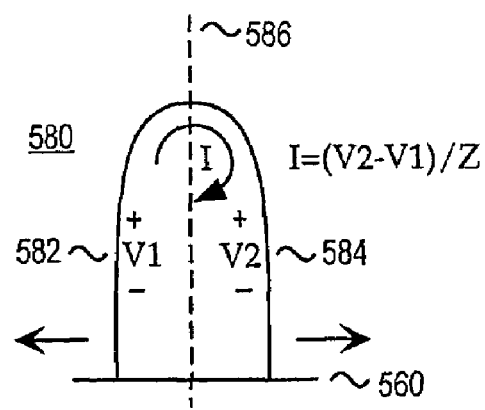
FIG. 5 illustrates an electrical model of a shorted coil where coil portions are at 180° mechanical angle about the spindle axis.

FIG. 5 illustrates an electrical model 580 of a single shorted coil of a radial bearing when the coil portions 582, 584 are at 180° mechanical angle from each other. A shorting disk or ring (electrical model element 560) may be used to couple coil portions at 180° from each other about the coil assembly. Assuming bearing poles of the same magnetic vector are also located at 180° mechanical angle, the net induced current, I, will be zero when the impeller is properly centered (V1=V2) because the same voltage is induced in each coil portion. As the impeller rotational axis 590 is displaced from the central axis of the spindle 586, a voltage differential develops (i.e., V1≠V2) thus creating a non-zero current. The generated current is a function of the pitch of the shorted coils, rotational speed, strength of the bearing magnets, amount of displacement of the impeller, and the impedance, Z, of the shorted coils.

One characteristic that describes the drive component of a pump motor is the number of poles associated with the rotor. Each pole represents a concentration of magnetic flux. Each pole may be a single magnet or a plurality of magnets arranged to provide a resultant magnetic flux vector. The motor windings are electrically activated to repulse or attract the poles, thus resulting in rotation of the motor rotor. Each mechanical cycle (i.e., 360° rotation) for the rotor will result in one or more electrical cycles depending upon the number of pole pairs. A four pole motor, for example, experiences two electrical cycles for each mechanical cycle (4 poles/2 poles per set).

The permanent magnets and shorted coils of the electrodynamic bearing are discussed independently of any magnets or windings used in the drive mechanism for the pump. Magnets used for the drive component of the pump are referred to as drive magnets or motor poles. Magnets used for the magnetic bearing are referred to as bearing magnets or bearing poles. Unless noted otherwise, subsequent use of the terms "magnets" and "coils" is referring to their use in the impeller bearing.

Each bearing pole may comprise a single magnet or a plurality of magnets. In one embodiment, the bearing poles have been arranged to form an "undulating magnet" or Halbach array. One advantage of a Halbach array is that the magnetic flux tends to be concentrated on a selected one of the interior or exterior of a cylindrical Halbach array or only on one side of a linear Halbach array. The individual poles making up the Halbach array also tend to result in a more sinusoidal magnetic field. Although the magnetic vectors defined by the Halbach array have different orientations, they need not be defined by completely distinct magnets. For example, a Halbach array may be created by creating domains of magnetization within a single element. In one embodiment, the Halbach array is created by magnetic strips of sintered NdFeB.

Figure 6:
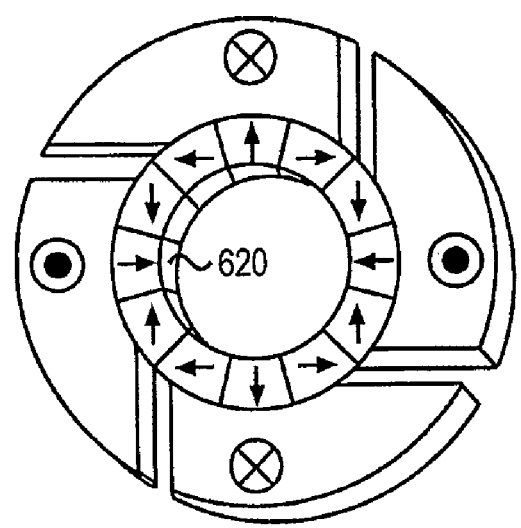
FIG. 6 illustrates an impeller hub having magnetic vectors organized to form a Halbach array through individual elements or individual magnetic domains.
Figure 6:
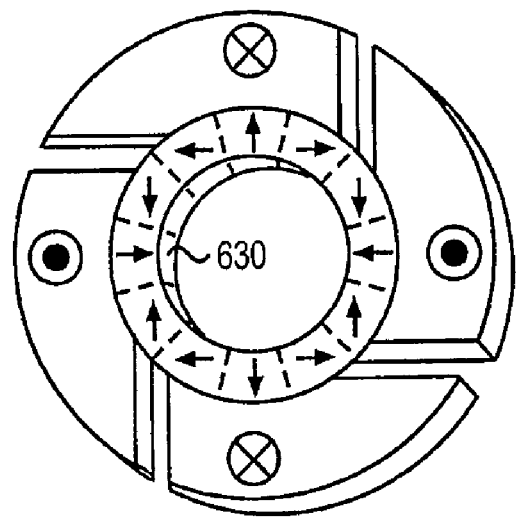

FIG. 6 illustrates the permanent magnet "hub" of a magnetic bearing comprising a Halbach array. The Halbach array of hub 620 is formed using separate magnetic elements wherein the magnetic vectors within each element are substantially the same throughout. The Halbach array of hub 630 is formed by varying the magnetization (i.e., individual magnetic domains) within a given element. Although each domain within hub 630 may have magnetic vectors substantially the same throughout, the individual domains may have magnetic vectors significantly different from each other within the same element. Individual domains within the same magnetic element are magnetized such that the domains collectively form a Halbach array.

Figure 7:
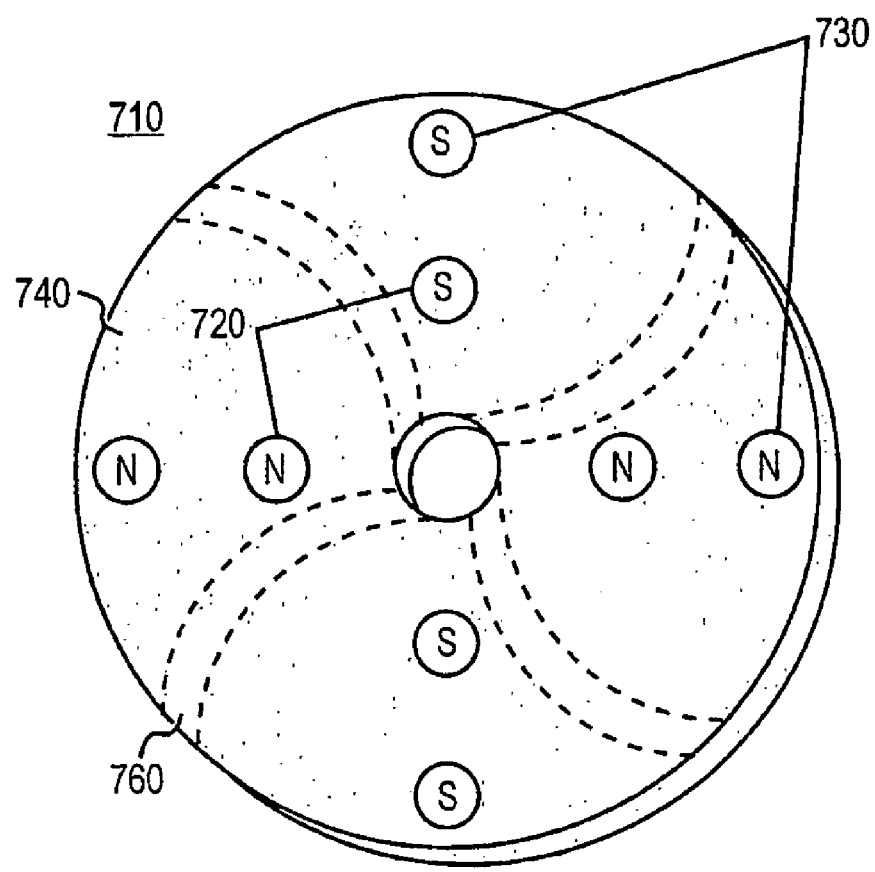
FIG. 7 illustrates one embodiment of an impeller configured for an axial flux gap motor and an axial electrodynamic bearing.

FIG. 7 illustrates one embodiment of an impeller 710 configured for an axial flux gap motor and an axial electrodynamic bearing. The permanent magnets forming the bearing poles may be coupled to a selected one of the stator or the impeller. The shorted coils are located with the other of the stator or the impeller. In the illustrated embodiment, the magnets forming bearing poles 720 and the magnets forming motor poles 730 are disposed within vanes 740 of the impeller 710. Disk shaped impeller 710 includes a plurality of channels 760 for moving the working fluid of the pump. In the illustrated embodiment, each channel is formed on only one face of the impeller so that the channels do not extend to or connect both faces of the impeller. The axial flux gap motor architecture and the axial electrodynamic bearing design indicate that the axis of magnetization of the motor poles and the bearing poles are parallel to an impeller axis of rotation.

In the illustrated embodiment, the bearing poles 720 are distinct from the motor poles 730. The bearing and motor poles do not have any magnetic elements in common. The number of bearing poles may be less than, equal to, or greater than the number of motor poles when the bearing poles are distinct from the motor poles.

In an alternative embodiment, the bearing poles and motor poles rely on the same magnetic elements. One end of each magnet forms a motor pole for the motor drive component and the other end of the magnet serves as a bearing pole for the impeller support. This might be the case, for example, with an axial flux gap motor having an axial electrodynamic bearing or a radial flux gap motor having a radial electrodynamic bearing. Given that one end of the magnets serves as a motor pole and the other end serves as a bearing pole, the motor will typically be limited to stator windings only at one end of the magnets.

Although the bearing poles 720 are indicated as being closer to the inner periphery of the impeller while the motor poles are located closer to the outer periphery of the impeller, other embodiments are possible. For example, in one embodiment the pump motor and electrodynamic bearings architecture is defined such that poles 720 are the motor poles and poles 730 are the bearing poles. In this alternative embodiment, the motor poles are closer to the inner periphery of the impeller while the bearing poles are closer to the outer periphery of the impeller.

Figure 8:
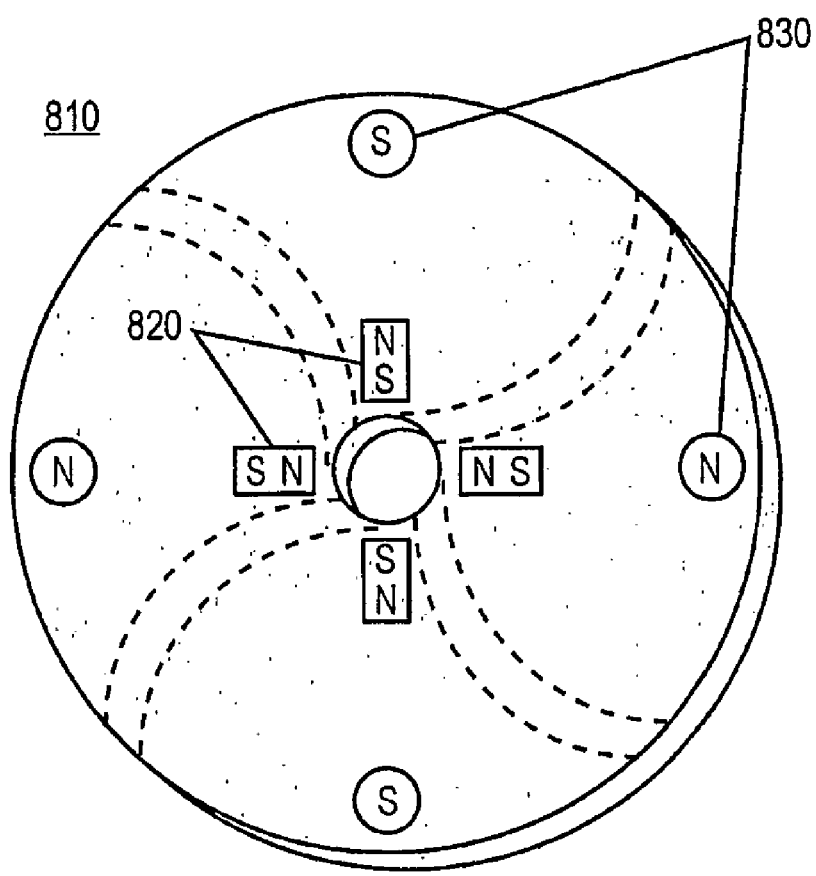
FIG. 8 illustrates one embodiment of an impeller configured for an axial flux gap motor and a radial electrodynamic bearing.

FIG. 8 illustrates one embodiment of an impeller 810 configured for an axial flux gap motor and a radial electrodynamic bearing. The axis of magnetization of the motor poles 830 is parallel to the impeller axis of rotation, but the axis of magnetization of the bearing poles 820 are perpendicular to the impeller axis of rotation. In this embodiment, the number of bearing poles is the same as the number of motor poles. Due to the use of distinct magnetic elements for bearing and motor poles, the motor architecture may incorporate either a single or dual stator (i.e., a set of drive windings for each end of the motor poles). Thus, for example, stator windings may be incorporated into the top and bottom housing portions to produce a dual stator axial gap motor architecture.

Figure 9:
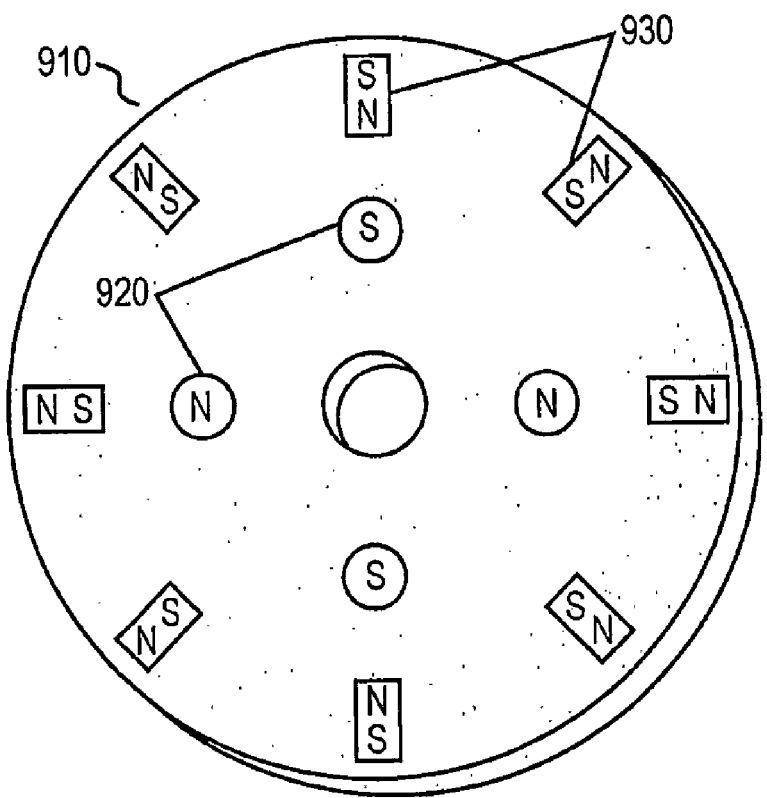
FIG. 9 illustrates one embodiment of an impeller configured for a radial flux gap motor and an axial electrodynamic bearing.

FIG. 9 illustrates one embodiment of an impeller 910 configured for a radial flux gap motor and an axial electrodynamic bearing. The axis of magnetization of the motor poles is perpendicular to the impeller axis of rotation, but the axis of magnetization of the bearing poles is parallel to the impeller axis of rotation. In this embodiment, the number of bearing poles is not the same as the number of motor poles. Impeller 910 has 8 motor poles 930 and 4 bearing poles 920.

Figure 10:
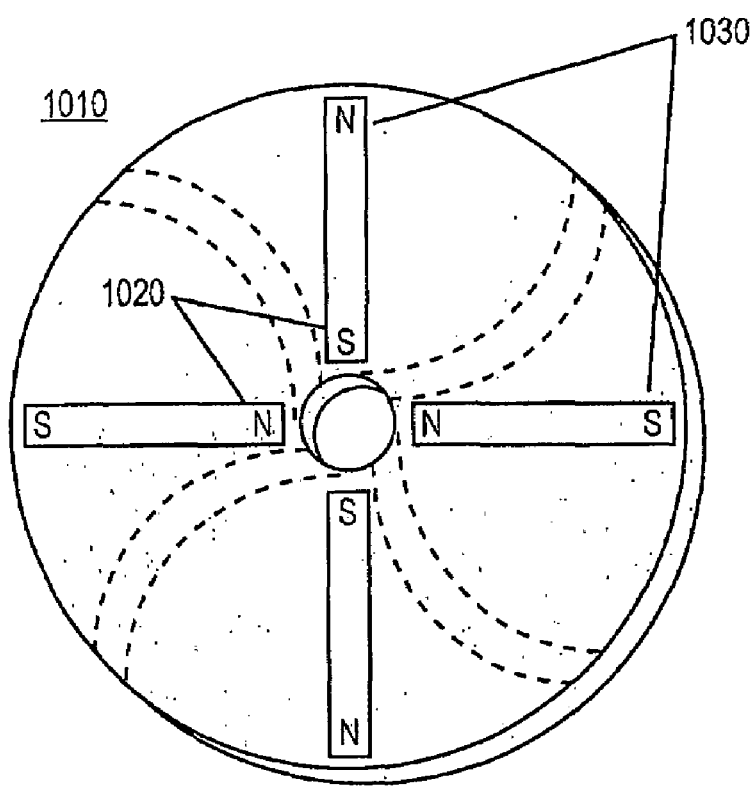
FIG. 10 illustrates one embodiment of an impeller configured for a radial flux gap motor and a radial electrodynamic bearing.

FIG. 10 illustrates one embodiment of an impeller 1010 configured for a radial flux gap motor and a radial electrodynamic bearing. The radial flux gap motor architecture and the radial electrodynamic bearing design indicate that the axis of magnetization of the motor poles and the bearing poles are perpendicular to the impeller axis of rotation. In this embodiment, the motor poles and the bearing poles are at opposing ends of the same magnets. The motor windings may be located adjacent the outer periphery of the impeller (i.e., poles 1030) or the inner periphery of the impeller (i.e., poles 1020) depending upon the desired location for the drive portion of the motor. The shorted coils for the radial bearing are located adjacent the periphery not otherwise selected for the motor windings.

In the preceding illustrations, the bearing poles were located on the impeller. In alternative embodiments, however, the shorted coils are coupled to the impeller while the bearing poles are coupled to the stator. High energy magnets such as samarium cobalt or neodymium-iron-boron (NdFeB) may be used for the motor pole magnets, the bearing pole magnets, or both. Regardless of whether the bearing poles are substantially the same as or distinct from the motor poles, the shorted coils may be arranged to achieve different forces as desired for the bearing.

Figure 11:
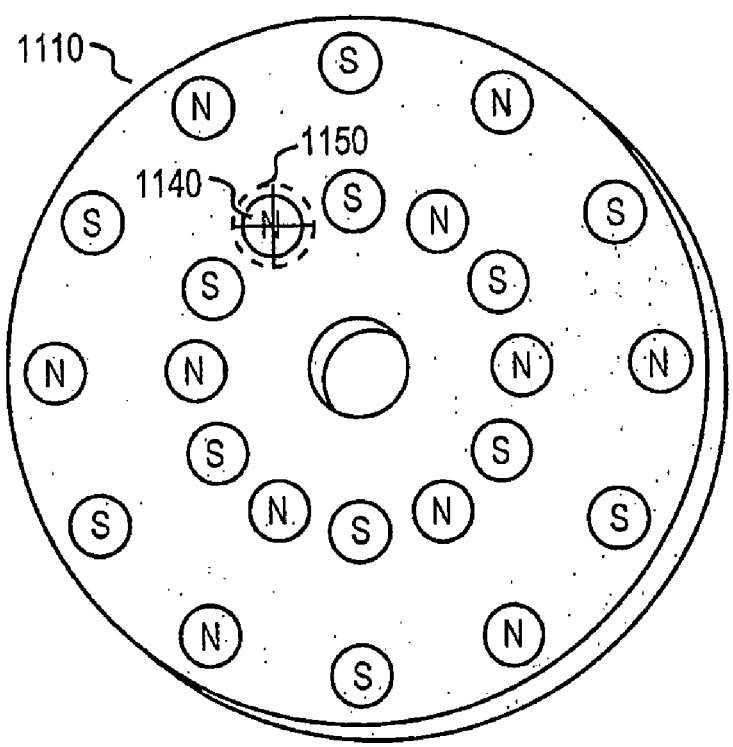
FIG. 11 illustrates repulsive forces contributed to an impeller by a single shorted coil when the coil is configured for induction from a single bearing pole at a time.

For example, each shorted coil may be arranged such that current is induced predominately by only a single bearing pole at any given point in time as is the case with the shorted coils of FIG. 3. FIG. 11 illustrates the axial repulsive force contributed to an impeller 1110 by a single shorted coil when the coil is configured for induction by a single bearing pole 1140 at a time. No blades or channels are illustrated in order to more clearly illustrate other features.

Each coil can only exert repulsive forces 1150 on the area of the inducing bearing pole 1140. Thus each coil can produce only a localized repulsive force on the impeller 1110. This repulsive force may be used to counteract any axial loading during pump operation. In this configuration each shorted coil has time varying currents in them at all times.

In another embodiment, each shorted coil is arranged such that current is induced by a selected plurality, k, of bearing poles. In such cases, the coil should be arranged so that the selected plurality of bearing poles have the same magnetic flux vector (i.e., same polarity or magnetization vector).

Figure 12:
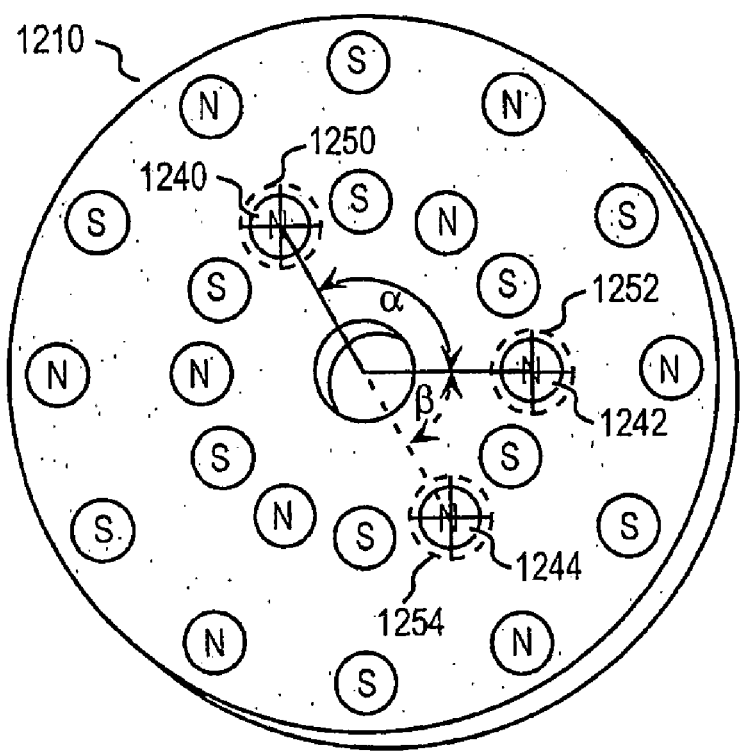
FIG. 12 illustrates repulsive forces contributed to an impeller by a single shorted coil when the coil is configured for induction by two bearing poles at a time.

FIG. 12 illustrates the repulsive forces contributed to an impeller by a single shorted coil when the coil is configured for induction by two bearing poles at a time (i.e., k=2). Each shorted coil is acted upon substantially simultaneously by a pair of bearing poles. Examples of bearing pole pairs at different mechanical angles ($\alpha$, $\beta$, $\alpha+\beta$) are illustrated. One pairing of bearing poles (1240, 1242) represents a mechanical angle $\alpha \approx 120°$. Another pairing of bearing poles (1242, 1244) represents a mechanical angle $\beta \approx 30°$. Yet another combination (1240, 1244) represents a mechanical angle $\alpha+\beta \approx 180°$.

The repulsive forces will now be distributed across two bearing poles instead of one. When the impeller is properly aligned, the bearing poles induce the same current substantially simultaneously into the shorted coil. Thus the repulsive force is equally distributed among each bearing pole of the bearing pole pair.

As the mechanical angle between bearing pole pairs increases, the current differential for the same angular displacement also increases. Thus increasing the mechanical angle tends to increase the bearing's effectiveness. This current differential results in an unequal distribution of repulsive forces across the bearing poles. The unequal distribution of force makes it easier for the impeller to be returned to the correct position in the presence of an opposing restoring force. The coils will have time varying currents in them whenever the impeller is incorrectly positioned.

The optimal mechanical angle between bearing poles when each coil interacts with only two bearing poles at a time is 180° (the simultaneously inducing bearing poles have the same magnetization vector). If the electrodynamic bearing is designed so that the same magnitude of current is induced into the shorted coil by each bearing pole when the impeller is centered, there will be no net current flow in the shorted coil due to the opposing signs. Zero current flow results in less heat dissipation for the pump which may be particularly desirable in implantable pump applications such as blood pumps. When the impeller is properly centered this implies that the pump will be more energy efficient because energy from the rotating impeller will not be consumed by the magnetic bearing.

Figure 13:
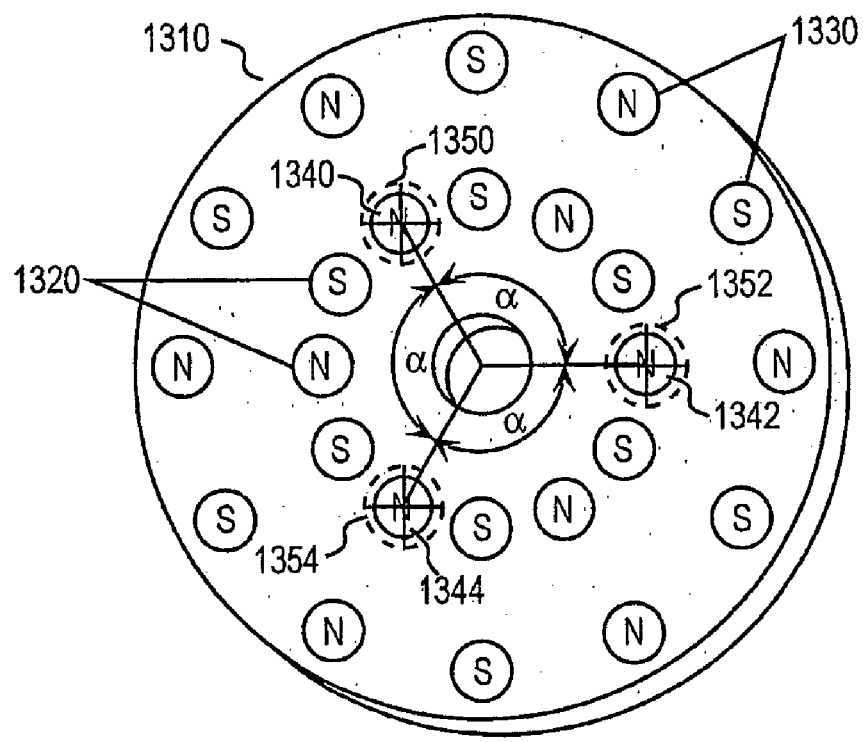
FIG. 13 illustrates repulsive forces contributed to the impeller by a single shorted coil when the coil is configured for induction by a plurality of bearing poles at a time.

FIG. 13 illustrates repulsive forces applied to the impeller by a single shorted coil when the coil is configured for simultaneous induction by a selected plurality, k, of bearing poles at any given time where k>2. In one embodiment, each shorted coil is configured so that the selected plurality of bearing poles (1340, 1342, 1344) are at relative equidistant mechanical angles. The k bearing poles are thus distributed about the axis of rotation at mechanical angles of $$\frac{2\pi}{k}$$

radians (i.e., $$\left(\text{i.e., } \frac{360°}{k}\right).$$

This distributes the repulsive forces (1350, 1352, 1354) about the impeller axis of rotation. "Ripples" or variations in the forces supporting the impeller may be reduced by increasing the number k and configuring the shorted coil so that the k selected bearing poles are distributed in this manner.

The control of an impeller requires control of 6 degrees of freedom of motion. The bearings must account for 5 degrees of freedom while 1 degree of freedom is allocated to the drive component for handling the rotational velocity of the impeller. A radial or axial electrodynamic bearing can be used in conjunction with other bearings for full control of the impeller. The use of the electrodynamic bearing to reduce the number of degrees of freedom over which control must still be exerted, for example, reduces the computational complexity required by an AMB. Alternatively, the electrodynamic bearing may be used with other passive bearing mechanisms. Thus in one embodiment, an impeller is configured for both an axial electrodynamic bearing and a radial electrodynamic bearing.

Figure 14:
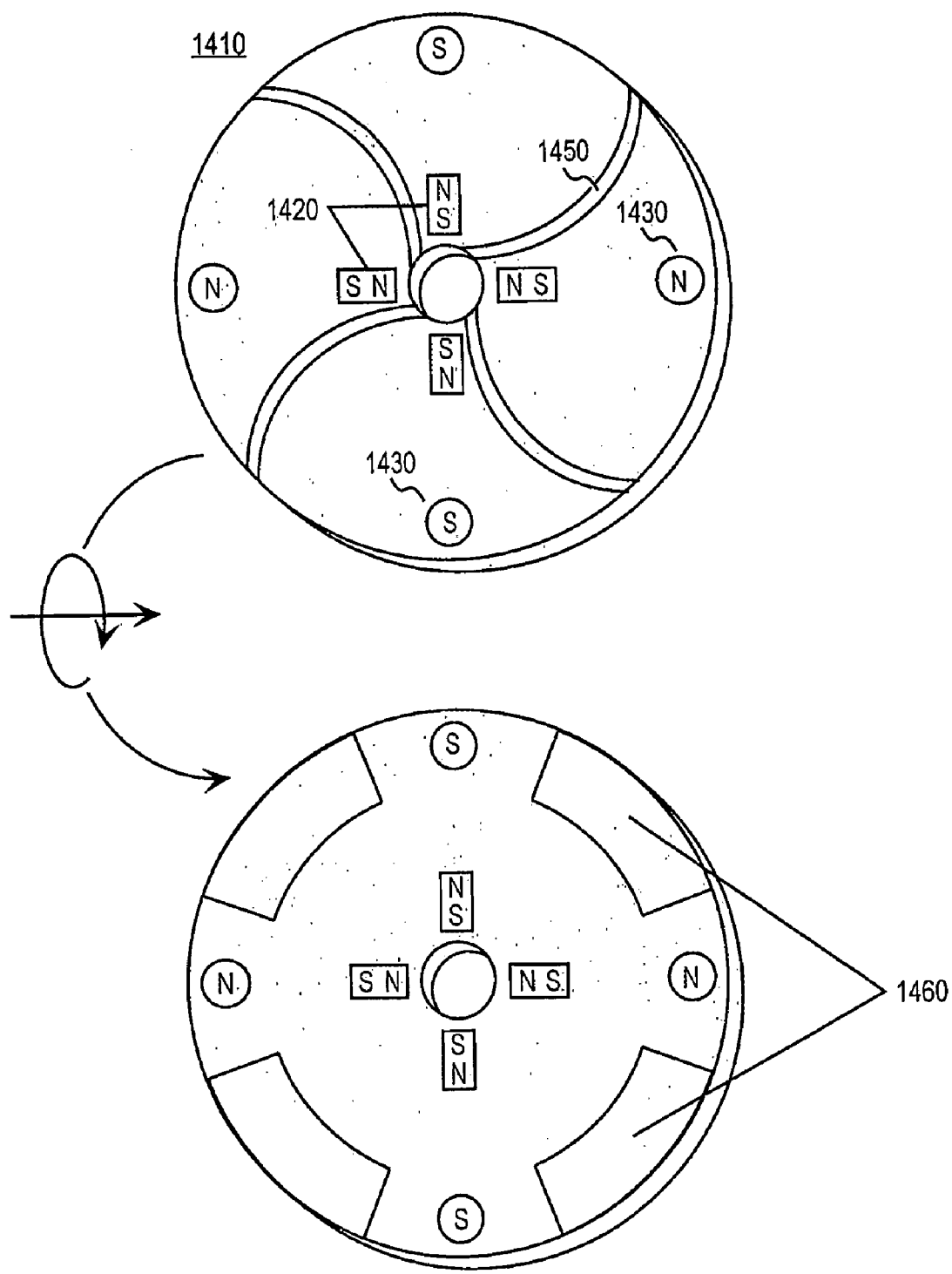
FIG. 14 illustrates an impeller with a radial electrodynamic bearing and an axial hydrodynamic bearing surface.

FIG. 14 illustrates one embodiment of an impeller 1410 designed for a centrifugal pump with an axial flux gap motor architecture as indicated by the configuration of motor poles 1430. The impeller 1410 includes a plurality of bearing poles 1420 (or alternatively shorted coils) for a radial electrodynamic bearing. In this embodiment, the impeller includes a plurality of blades 1450 on one face of the impeller. In addition, the impeller may have hydrodynamic bearing surfaces 1460 designed to generate axial or radial hydrodynamic bearings when the bearing becomes too close to features of the stator such as a diffuser or a volute wall. The hydrodynamic bearings may be realized by providing regions 1460 on one face of the impeller that have tapered surfaces, for example. In this example, an axial hydrodynamic bearing can form between the stator and rotor or impeller as indicated at 306 of FIG. 3 when the face with the tapered surfaces is rotating in close proximity to the volute wall of the stator. Instead of "blades" the impeller may use a plurality of channels to move the working fluid. In one embodiment, the channels or blades are located only on one face of the impeller.

Although the illustrations are directed towards an impeller for a centrifugal pump, the electrodynamic bearing can be used with other pump architectures such as axial flow or mixed flow pumps. Moreover, the pump architecture may include either radial, axial, or both types of electrodynamic bearings. The electrodynamic bearings may be utilized in pumps incorporating either axial or radial flux gap motor architectures.

The use of electrodynamic bearings is an improvement over contact bearings which tend to damage some working fluids such as blood (e.g., thrombosis, hemolysis). If needed, the impeller may be coated to protect the impeller and incorporated elements from the working fluid. The electrodynamic bearings may also be used for pump applications where the working fluid is gaseous or otherwise fluid-like (e.g., mixtures) in nature. For example, air blowers or fans may benefit from the electrodynamic bearing due to the lack of any need for bearing lubrication. Given that the bearing is operable only once the rotational speed reaches a threshold, the designer may need to incorporate touchdown bearings or other mechanisms to prevent damage when transitioning from an "off" state to an "on" state or from rotational speeds above the threshold to rotational speeds below the threshold. For applications where the pump is designed to run continuously (i.e., blood pumps), such touchdown bearings may not be necessary as a practical matter.

In the preceding detailed description, the invention is described with reference to specific exemplary embodiments thereof. Various modifications and changes may be made thereto without departing from the broader spirit and scope of the invention as set forth in the claims. The specification and drawings are, accordingly, to be regarded in an illustrative rather than a restrictive sense.

The invention claimed is:

1. An apparatus comprising:
   a rotor;
   a stator;
   a plurality of permanent magnets forming bearing poles coupled to a selected one of the stator and the rotor; and
   a plurality of shorted coils coupled to the other of the stator and the rotor, wherein the plurality of bearing poles and shorted coils co-operate to form an electrodynamic bearing during rotation of the rotor, wherein at least one of the stator and the rotor includes hydrodynamic bearing surfaces for generating a hydrodynamic bearing between the rotor and stator.

2. The apparatus of claim 1 wherein the plurality of permanent magnets is carried by the rotor and the plurality of shorted coils is coupled to the stator.

3. The apparatus of claim 1 wherein the electrodynamic bearing forms an axial bearing.

4. The apparatus of claim 1 wherein the electrodynamic bearing forms a radial bearing.

5. The apparatus of claim 1 wherein the hydrodynamic bearing forms a radial bearing.

6. The apparatus of claim 1 wherein the hydrodynamic bearing forms an axial bearing.

7. The apparatus of claim 1 wherein the plurality of permanent magnets comprises a plurality of distinct magnetic elements, each magnetic element corresponding to one of the bearing poles.

8. The apparatus of claim 7 wherein the individual magnetic elements form a Halbach array.

9. The apparatus of claim 1 wherein the plurality of permanent magnets is a single element comprising a plurality of distinct magnetic domains, each magnetic domain corresponding to one of the bearing poles.

10. The apparatus of claim 9 wherein the plurality of magnetic domains forms a Halbach array.

11. The apparatus of claim 1 wherein the stator further comprises a spindle about which the rotor rotates.

12. The apparatus of claim 1 wherein the rotor includes a plurality of tapered surfaces for generating the hydrodynamic bearing.

13. The apparatus of claim 1 wherein the apparatus further comprises a plurality of motor poles for driving the rotor, wherein the motor poles and bearing poles are distinct.

14. The apparatus of claim 13 wherein the number of bearing poles is distinct from the number of motor poles.

15. The apparatus of claim 1 wherein the plurality of permanent magnets also serve as motor poles for driving the rotor.

16. The apparatus of claim 1 wherein at least one bearing pole further comprises a plurality of permanent magnets.

17. The apparatus of claim 1 further comprising a plurality of motor poles for driving the rotor, wherein each of the motor poles has an axis of magnetization substantially parallel to an axis of rotation of the rotor.

18. The apparatus of claim 1 further comprising a plurality of motor poles for driving the rotor, wherein each of the motor poles has an axis of magnetization substantially perpendicular to an axis of rotation of the impeller.

19. The apparatus of claim 1 wherein the rotor further comprises an impeller.

* * * * *